US008388593B2

(12) United States Patent
Mavinkurve et al.

(10) Patent No.: US 8,388,593 B2
(45) Date of Patent: Mar. 5, 2013

(54) FLUID MANAGEMENT ARTICLE HAVING BODY-FACEABLE PROTRUSIONS

(75) Inventors: Pramod S. Mavinkurve, Princeton, NJ (US); John T. Ulman, Woodbridge, NJ (US); Steven H. White, Flemington, NJ (US); Robert J. Graeme, III, Morrisville, PA (US); Kenneth Anthony Pelley, Hopewell, NJ (US); Brian Michael Drzewiecki, Princeton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 1466 days.

(21) Appl. No.: 10/459,921

(22) Filed: Jun. 12, 2003

(65) Prior Publication Data

US 2004/0254554 A1 Dec. 16, 2004

(51) Int. Cl.
*A61F 13/15* (2006.01)
*A61F 13/20* (2006.01)

(52) U.S. Cl. .................. 604/385.101; 604/380
(58) Field of Classification Search .................. 604/380, 604/395; 428/163, 169, 184–186
See application file for complete search history.

(56) References Cited

U.S. PATENT DOCUMENTS

| | | | | |
|---|---|---|---|---|
| 3,530,023 A * | 9/1970 | Roberts, Jr. et al. | .......... | 156/290 |
| 4,381,783 A | 5/1983 | Elias | | |
| 4,392,862 A * | 7/1983 | Marsan et al. | ................ | 604/366 |
| 4,518,451 A | 5/1985 | Luceri et al. | | |
| 6,436,082 B1 | 8/2002 | Mizutani et al. | | |
| 6,525,239 B2 * | 2/2003 | Cole | ............................ | 604/382 |
| 6,673,418 B1 * | 1/2004 | DeOlivera et al. | ............. | 428/171 |
| 2002/0065498 A1 * | 5/2002 | Ohashi et al. | ................. | 604/379 |
| 2002/0143309 A1 * | 10/2002 | Glasgow et al. | .............. | 604/378 |
| 2003/0088222 A1 * | 5/2003 | Yoshimasa et al. | ........... | 604/380 |
| 2004/0081804 A1 * | 4/2004 | Basler et al. | .................. | 428/174 |
| 2006/0122572 A1 * | 6/2006 | Suarez | ................... | 604/385.101 |

FOREIGN PATENT DOCUMENTS

| | | |
|---|---|---|
| CN | 2237435 Y | 10/1996 |
| CN | 1397261 A | 2/2003 |
| EP | 1 022 003 A1 | 12/1999 |
| EP | 1 090 615 A1 | 4/2001 |
| EP | 1 103 240 A1 | 5/2001 |
| EP | 1103240 A1 * | 5/2001 |
| EP | 1 275 358 A2 | 1/2003 |
| EP | 1 346 712 A1 | 9/2003 |
| EP | 1638495 B1 | 12/2009 |

\* cited by examiner

*Primary Examiner* — Melanie Hand

(57) ABSTRACT

A fluid-management article, such as a sanitary napkin, comprises a body-faceable, liquid-pervious cover having a top surface, a garment-faceable, liquid-impervious barrier, and an absorbent system intermediate the cover and the barrier. The fluid-management article comprises a plurality of fluid-guiding channels that surround a plurality of isolated protrusions. The channels and the protrusions are formed through the top surface of the cover of the fluid management article. The protrusions have an apex that extends a height greater than about 0.5 millimeters (mm) above at least a portion of the plurality of channels. The protrusions have a number density greater than about 0.15 protrusions/cm$^2$.

28 Claims, 8 Drawing Sheets

FLUID MANAGEMENT ARTICLE HAVING BODY-FACEABLE PROTRUSIONS

CROSS-REFERENCE TO RELATED APPLICATIONS

This patent application is related to the patent application entitled, "Thin Sanitary Napkin Having Protrusions," U.S. application Ser. No. 10/460,003, filed concurrently on Jun. 12, 2003, commonly assigned, and incorporated by reference in its entirety.

BACKGROUND OF THE INVENTION

1. Field of the Invention

The present invention generally relates to absorbent articles, and more particularly to absorbent articles having protrusions that are adapted to face and be positioned proximate or in contact with the body of the wearer of the article, in use.

2. Background of the Related Art

Disposable absorbent articles that comprise absorbent materials are disclosed in the literature are commercially available. Typical disposable absorbent articles include a body-faceable cover layer designed to keep the body dry, an absorbent system that generally holds and contains the bulk of any bodily discharges (e.g. blood, menses, urine, etc.), and a liquid-impervious barrier layer that prevents any bodily discharges from leaking out of the absorbent article.

Sanitary napkins, one type of disposable absorbent article, are worn by females in an undergarment adjacent to the pudendal region and which is intended to absorb and contain various exudates which are discharged from the body (e.g., blood, menses, urine, and the like) and which is intended to be discarded after a single use (i.e., it is not intended to be laundered or otherwise restored or reused).

Unfortunately, typical disposable absorbent articles such as sanitary napkins are limited in their capability to rapidly absorb liquid discharges. In particular, it is difficult for typical absorbent articles to absorb these discharges quickly and to prevent these discharges from being re-released from the article due to stresses upon the article from the body, etc. Accordingly, a need exists for a sanitary napkin that overcomes the above-mentioned drawbacks.

SUMMARY OF THE INVENTION

A fluid-management article, such as a sanitary napkin, comprises a body-faceable, liquid-pervious cover having a top surface, a garment-faceable, liquid-impervious barrier, and an absorbent system intermediate the cover and the barrier. The fluid-management article comprises a plurality of fluid-guiding channels that surround a plurality of isolated protrusions. The channels and the protrusions are formed through the top surface of the cover of the fluid management article. The protrusions have an apex that extends a height greater than about 0.5 millimeters (mm) above at least a portion of the plurality of channels. The protrusions have a number density greater than about 0.15 protrusions/cm$^2$.

According to another aspect of the invention, a method of forming a fluid management article comprises providing a body-faceable, liquid-pervious cover having a top surface, a garment-faceable, liquid-impervious barrier, and an absorbent system. The absorbent system is positioned intermediate the body-faceable, liquid-pervious cover and the garment-faceable, liquid-impervious barrier. A plurality of fluid-guiding channels are formed. The fluid-guiding channels define therebetween a plurality of isolated protrusions. The plurality of fluid-guiding channels and the plurality of isolated protrusions are formed through the top surface of the cover layer. The protrusions each have an apex that extends a height that is greater than about 0.5 mm above the plurality of channels.

BRIEF DESCRIPTION OF THE DRAWINGS

A more particular description of the invention, briefly summarized above may be had by reference to the embodiments thereof that are illustrated in the appended drawings. It is to be so noted, however, that the appended drawings illustrate only typical embodiments of the invention and, therefore, are not to be considered limiting of its scope, for the invention may admit to other equally effective embodiments.

FIG. 2 is a fragmented, top perspective view of the sanitary napkin of FIG. 1a;

FIG. 3 is a fragmented, cross-sectional view of the sanitary napkin of FIG. 1a taken through line 2-2 of FIG. 1a;

FIG. 4 is a cross-sectional view of a protrusion of the sanitary napkin of FIG. 1a;

To facilitate understanding identical reference elements have been used, wherever possible, to designate identical elements that are common to the figures.

DETAILED DESCRIPTION

The present invention generally relates to disposable absorbent articles such as sanitary napkins, pantiliners, absorbent products for incontinence, and other disposable absorbent articles worn close to a wearer's body. As used herein, the term "sanitary napkin" refers to an article which is worn by females in an undergarment adjacent to the pudendal region and which is intended to absorb and contain various exudates which are discharged from the body (e.g., blood, menses, urine, and the like) and which is intended to be discarded after a single use (i.e., it is not intended to be laundered or otherwise restored or reused). Pantiliners are generally similar to sanitary napkins, except that they typically have lower capacity for absorbing fluids and are generally used to control non-menstrual discharges. Both sanitary napkins and pantiliners are typically attached or secured to a users undergarment and positioned between the undergarment and wearer's pudendal region. Adult incontinence articles, diapers, and interlabial devices are yet other disposable absorbent articles designed to manage various bodily exudates and may benefit from the embodiments of the invention described herein.

Figure 1A:
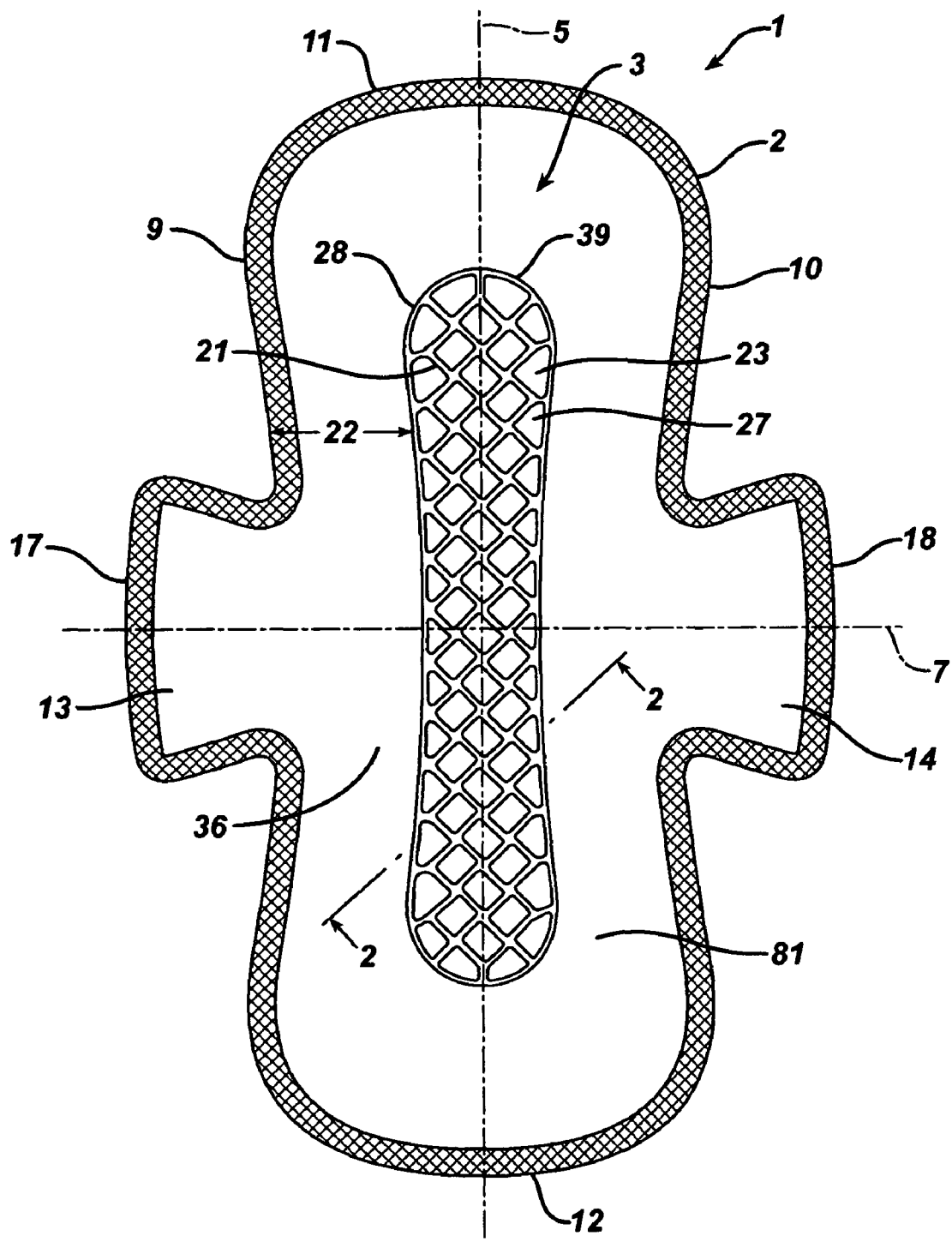
FIG. 1a is a plan view of a sanitary napkin consistent with embodiments of the invention described herein.

A specific implementation of a sanitary napkin 1 in accord with embodiments of the invention described herein is illustrated in FIG. 1a. The sanitary napkin 1 has a footprint boundary 2 that, when viewed from above, as shown in FIG. 1a, defines the spatial boundaries of the sanitary napkin 1. The footprint boundary 2 generally includes a first longitudinally-extending side edge 9, a second longitudinally-extending side edge 10 that is opposite the first longitudinally-extending side edge 9, a first transversely-extending end 11, and a second transversely-extending end 12. The sanitary napkin 1 is characterized as having an imaginary longitudinally-extending centerline 5 and an imaginary transversely-extending centerline 7 that is generally perpendicular to the longitudinally-extending centerline 5 (the longitudinally-extending centerline 5 and the transversely-extending centerline 7 are shown in phantom in FIG. 1a).

The sanitary napkin 1 has a main body 3. In one embodiment of the invention, the footprint boundary 2 is substantially symmetric about the longitudinally-extending centerline 5. Flaps 13, 14 optionally adjoin the main body 3 and extend laterally outward (i.e., away from the longitudinally extending centerline 5) therefrom. The flaps 13, 14 extend to respective distal edges 17, 18.

Figure 2:
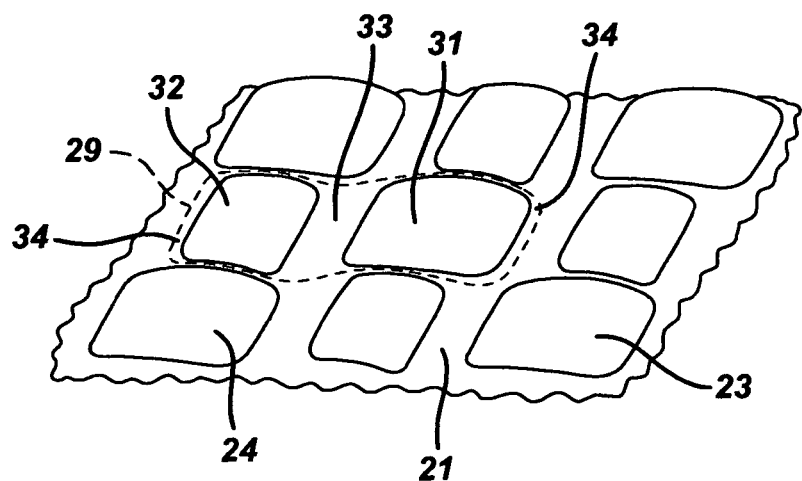

Referring to FIG. 1a as well as FIG. 2, the sanitary napkin 1 includes a plurality of fluid-guiding channels 21, the fluid-guiding channels 21 defining therebetween a plurality of protrusions 23. The fluid-guiding channels 21 and the protrusions 23 are formed through a top surface 81 of the sanitary napkin 1. When the sanitary napkin 1 is worn by a user, the protrusions 23 are positioned proximate (or in contact with) and facing the wearer's body.

Note that the terms "above," "top," "bottom," "below," etc. are used in this specification to denote relative positions among various features of the sanitary napkin 1, particularly when the sanitary napkin 1 is placed on a flat surface and oriented such that the protrusions 23 project above the channels 21.

Figure 1B:
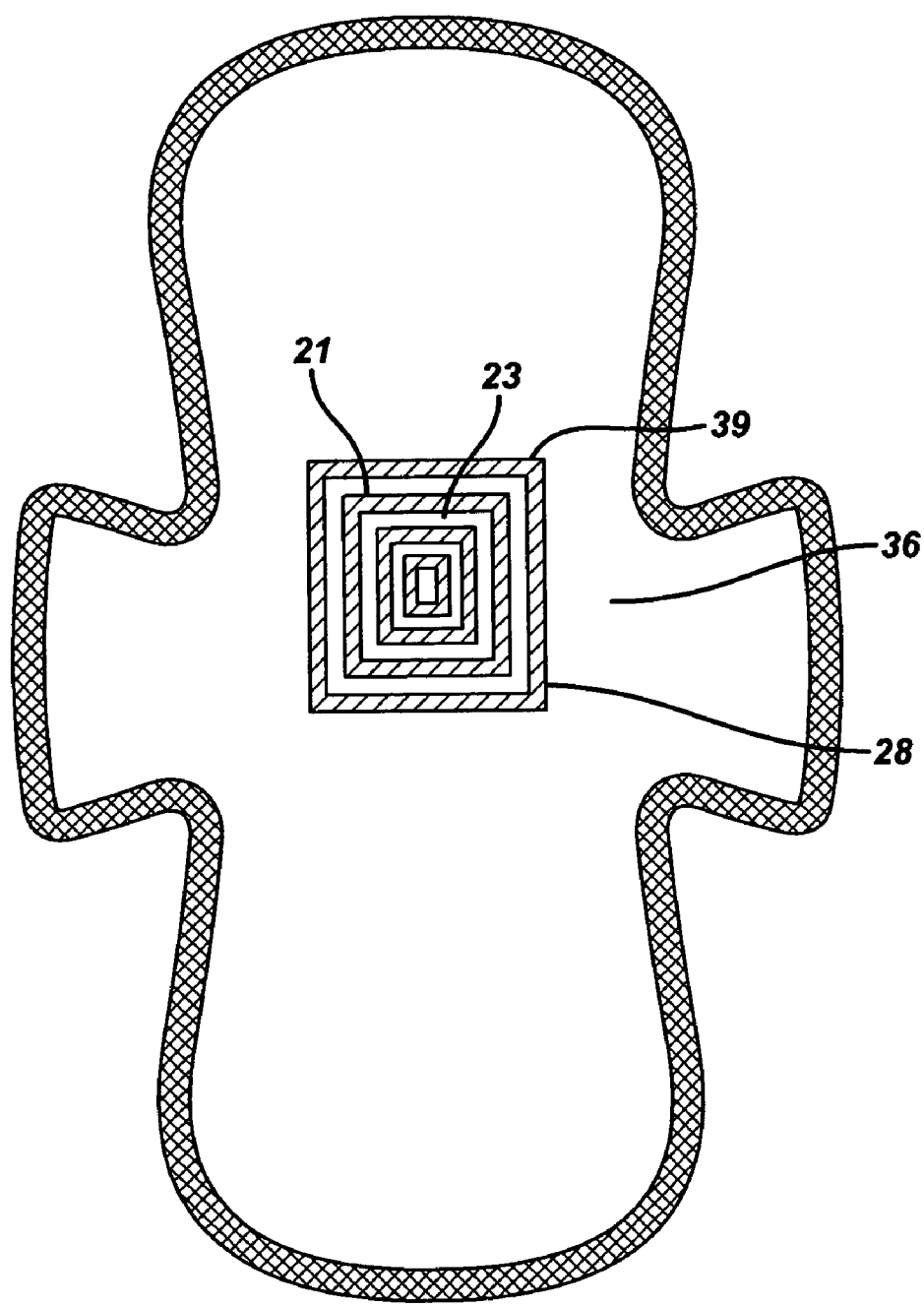
FIG. 1b is a plan view of an alternative embodiment of the sanitary napkin of the present invention.

The protrusions 23 are isolated. By isolated it is meant that each individual protrusion 23 is completely surrounded by at least one of the plurality of channels 21. The channels 21 that completely surround each protrusion 23 are generally regions of lesser height that may be of higher compression or higher density than the protrusion 21 that is surrounded. The channels 21 that surround each protrusion 23 may be disconnected from other neighboring channels 21 (as shown in FIG. 1b). Alternatively, the plurality of channels 21 are connected so as to form a continuous network that defines at least two adjacent protrusions 23 and interconnects the protrusions 23 (as shown in FIG. 1a). In this latter embodiment of the invention, if one were to imagine the channels 21 as canals filled with water, by starting from any one of the channels 21 and by moving along one or more paths through the plurality of channels 21, one could reach a boundary 35 (shown in FIG. 3) of any of the protrusions 23. The protrusions 23 extend above the plurality of channels 21. In particular, each protrusion 23 extends above at least a portion of channels 21 that surround the protrusion 23.

In the embodiment of the invention depicted in FIG. 1a, the plurality of protrusions 23 extend to an outer boundary 28 that separates a continuous region 27 of the protrusions 23 and the channels 21 from an external region 36 that is generally free of the protrusions 23 and fluid guiding channels 21 described above. The continuous region 27 preferably extends across a central portion of the sanitary napkin 1. The continuous region 27 may be spaced apart from the footprint boundary 2 of the sanitary napkin 1 a distance 22 that is in a range from about 5 mm to about 20 mm.

In one embodiment of the invention, the continuous region 27 generally provides a region of the sanitary napkin 1 that has a high overall flexibility. The external region 36, may provide a region of high relative lateral stiffness. By centrally positioning the continuous region 27, the sanitary napkin 1 is able to flexibly follow the contours of the wearer' body (such that the protrusions are proximate or in contact with the body of a wearer of the sanitary napkin 1, in use), while the external region 36 provides sufficient strength and stability to the sanitary napkin 1.

A projected area of the protrusions 23 (i.e., the sum of the area of each protrusion within the continuous region 27 as projected onto a two dimensional surface, such as is shown in FIG. 1a) is greater than a projected area of the channels 21 (i.e., the sum of the area of each channel within the continuous region 27 as projected onto a two dimensional surface, such as is shown in FIG. 1a). In a preferred embodiment of the invention, a ratio of the projected area of the protrusions 23 to the projected area of the channels 21 is less than 10. In a further preferred embodiment, the ratio is in a range from about 3 to about 7. Ratios above 10 are less desirable in that the channels 21 occupy too small a portion of the projected area of the sanitary napkin 1 relative to the protrusions 23, thus reducing fluid penetration time of the sanitary napkin 1.

The channels 21 may be of uniform length or varying length. The plurality of channels 21 may further include a perimeter channel 39 that forms the outer boundary 28 of the continuous region 27 of the plurality of protrusions 23. The plurality of channels 21 and the plurality of protrusions 23 may have various orientations. In one embodiment of the invention, the plurality of channels 21 are oriented obliquely with respect to the longitudinally-oriented centerline 5.

The continuous region 27 preferably extends across the longitudinally-extending centerline 5 such that protrusions 23 and channels 21 exist on both sides of the longitudinally-extending centerline 5. Furthermore, the continuous region 27 may extend across the transversely-extending centerline 7.

The continuous region 27 may comprise a two dimensionally repeating pattern of channels 21 and protrusions 23. The repeating pattern may be characterized as having a unit cell 29 (the boundaries of the exemplary unit cell 29 are shown in phantom in FIG. 2). The unit cell 29, when projected in two dimensions generates the continuous region 27 of the protrusions 23.

In the embodiment of the invention depicted in FIGS. 1a and 2, the unit cell 29 is comprised of a wide rectangular protrusion 31, a narrow rectangular protrusion 32, a channel 33 separating the protrusion 31 from the protrusion 32, and additional channels (or portions of channels) 34 (shown in FIG. 2) surrounding the protrusions 31, 32. While FIG. 2 shows the protrusions 23 having upper surfaces 24 that are smooth and continuous, the upper surface 24 may include dimples, valleys, or depressions or otherwise exhibit substantial tortuosity. The shapes of the protrusions 23 are, however, not critical, and may be diamond-like, square, circular, triangular, among other shapes. Furthermore, while FIG. 1a depicts linear channels 21 that surround each protrusion 23, other shapes (e.g., arcuate, circular, etc.) are contemplated. In addition, the unit cell 29 need not comprise two protrusions 23 (i.e., the pattern may include any number of protrusions 23 in order to generate the continuous region 27).

Figure 3:
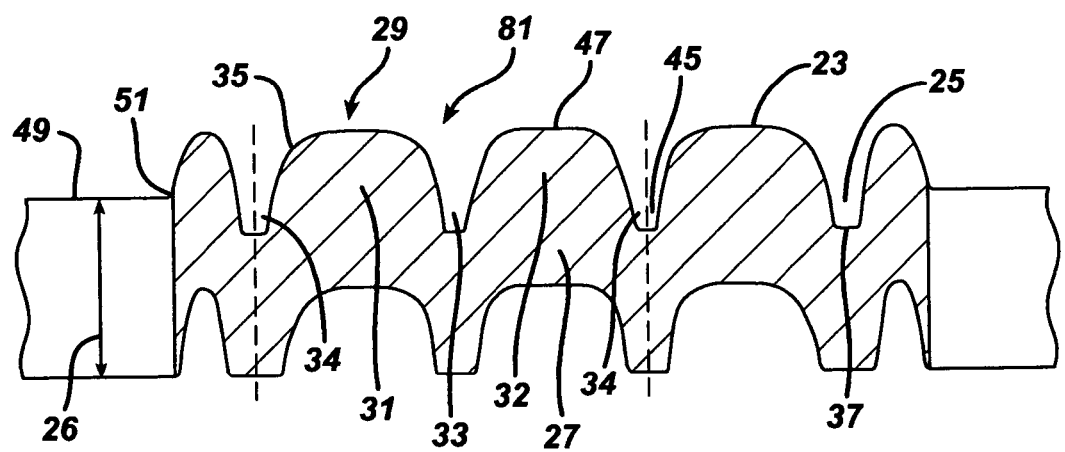

FIG. 3 depicts a fragmented, cross-sectional view of the sanitary napkin 1. FIG. 3 shows the protrusions 23 and the channels 21 formed through the top surface 81 of the sanitary napkin 1, as well as a two-dimensional representation of the unit cell 29 that can be used to generate the continuous region 27 of the protrusions 23 and the channels 21. It also shows the upper boundaries 35 of the protrusions 23 as well as a lower surface 45 of the channels 21. In addition, FIG. 3 also shows limits of the continuous region 27 (the continuous region 27 is cross-hatched in FIG. 3).

The protrusions 23 have an apex 47 that extends above a reference point 51. The reference point 51 is generally immediately outside the continuous region 27. The reference point 51 may lie within a reference plane 49 that defines the uppermost surface of a portion of the sanitary napkin 1 that is outside of the continuous region 27 of protrusions 23 and channels 21. In one embodiment of the invention, the lower surface 45 of the channels 21 resides below the reference point 51, or, alternatively, the lower surface 45 resides below the reference plane 49.

The channels 21 are generally shaped such that the lower surface 45 is flat or concave (i.e., when the sanitary napkin 1 is lain flat, the lower surface 45 is not continuously sloping downward). Thus, the channels 31 are capable of guiding fluid across the sanitary napkin. It is preferred that the lower surface 45 of the channels 21 is substantially flat and even. However, in one embodiment of the invention, the channels 21 have an undulating surface such as may be created by perforation or embossing of the channels 21 into one or more material layers of the sanitary napkin 1.

Preferably, within the continuous region 27, a lowermost point 37 on the lower surface 45 of the channels 21 is the lowermost surface within the continuous region 27 (i.e., in this embodiment, there are no depressions within the continuous region 27 that exist below the lowermost point 37 of the lower surface 45 of the channels 21). Stated in other words, the unit cell 29 does not, in this instance, include a depression below the lower surface 45 of the channels 21.

The sanitary napkin 1 has a caliper 26 that is the thickness of the sanitary napkin 1 as measured in an area outside the continuous region 27. If the continuous region 27 extends across the entire main body 3 of the sanitary napkin 1, the caliper 26 is the thickness of the sanitary napkin 1 averaged across the main body 3. The caliper 26 is measured when the sanitary napkin 1 is in a relaxed, uncompressed state, secured to prevent curling up of the edge (such as by using 2 lb. weights across the edges 9,10 and ends 11,12 to flatten the sanitary napkin 1), with release paper removed, and is measured in a region that encompasses all material layers of the sanitary napkin 1. The caliper 26 may be selected based upon desired technical properties of the sanitary napkin 1 (e.g. absorbency) or based upon consumer preference. In one embodiment of the invention, the caliper 26 is less than about 5 mm. In a further preferred embodiment, the caliper 26 less than about 3.5 mm.

Figure 4:
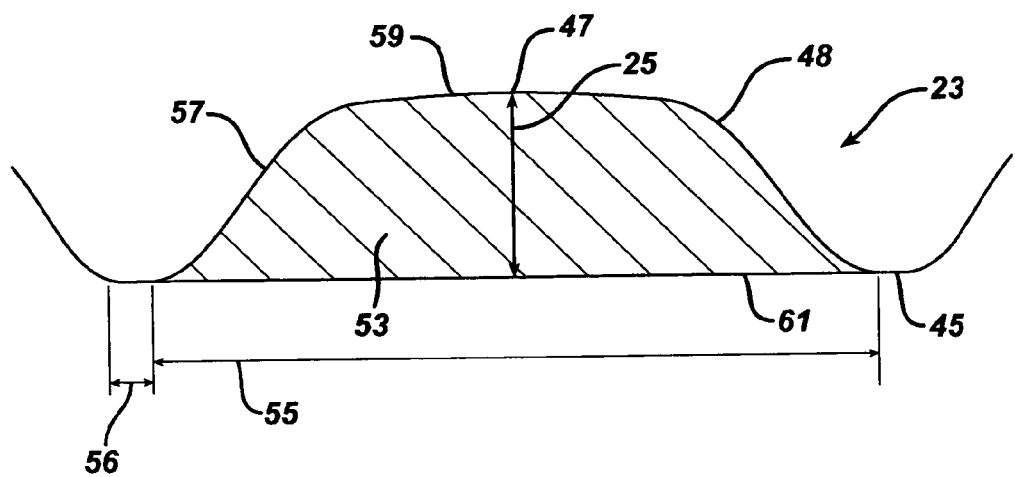

The protrusions 23 have a shape that is variable. In one embodiment of the invention, as shown in FIG. 4, the protrusions 23 are mesa-shaped. In other words, the protrusions 23 have a substantially flat or slightly rounded top portion 59 (providing comfort to a wearer of the sanitary napkin 1) and a substantially steeper, rounded edge 57 to facilitate the flow of bodily fluid towards the lower surface 45 of the channels 21.

The apex 47 of the protrusions 23 extends a height 25 above at least a portion of the lower surface 45 of the channels 21 that is greater than about 0.5 mm. The inventors have found that this distance is generally sufficient to maintain a gap between the lower surface 45 (not shown in FIG. 1a) of the channels 21 and a surface of the wearer's body. In another embodiment, the height 25 is in a range from about 0.5 mm to about the caliper 26 of the sanitary napkin 1. In another embodiment, the height 25 is in a range from about 0.75 mm to about 1.5 mm.

In one embodiment of the invention, the protrusions 23 have an individual width 55 greater than about 2 mm. In a preferred embodiment of the invention, the protrusions 23 have an individual width 55 that is selected based upon, for example, a dimension of a body orifice (e.g., an average vaginal opening dimension for a sanitary napkin) over which the sanitary napkin 1 is placed. For example, the individual width 55 of the protrusions 23 may be less than about 70 mm (70 mm is less than a typical distance between an anterior vaginal wall and a posterior vaginal wall of an average wearer of a sanitary napkin). In a further preferred embodiment of the invention, the individual width 55 of the protrusions 23 is between about 2 mm and about 35 mm. While the individual width 55 is depicted in FIG. 4 as the linear extent of the protrusion 23 in one dimension, the width 55 of the protrusion 23 is calculated as projected area of the protrusion 23 divided by a length of the protrusion, wherein the length is greatest distance between any two points on the protrusion. For a detailed description of a suitable method of determining the width of a protrusion, the reader is directed to patent application, "Thin Sanitary Napkin Having Protrusions," incorporated by reference and noted previously under CROSS-REFERENCE TO RELATED APPLICATIONS.

In order to provide sufficient guiding of fluid, the protrusions 23 have a number density greater than about 0.15 protrusions per $cm^2$. In one embodiment of the invention, the protrusions 23 have a number density greater than about 0.25 protrusions per $cm^2$ to about 25 protrusion per $cm^2$. In a further preferred embodiment of the invention, the protrusions 23 have a number density between about 1 protrusion per $cm^2$ to about 4 protrusions per $cm^2$. The number density of protrusions is calculated by taking the number of protrusions 23 and dividing this number by the projected area of the protrusions, i.e., the area of the protrusions projected onto the reference plane 49, shown in FIG. 3).

While the continuous region 27 is generally flexible in bending, the individual protrusions 23 of the sanitary napkin 1 are generally resistant to substantial deformation from the compression forces that are typically present during use, e.g., from about 10 to about 20 pounds per square inch for a sanitary napkin. As such, the protrusions 23 have sufficient resilience, even when wet, to maintain a separation between the lower surface 45 of the channels 21 and surfaces of the wearer's body that may be in contact with the protrusions 23. Furthermore, the protrusions 23 may be substantially nonelastic when subject to compression forces that are typical of those encountered in use.

In one embodiment of the invention, the sanitary napkin 1 has a stiffness, as measured by MODIFIED CIRCULAR BENDING, measured within the continuous region 27, that is greater than about 300 grams. In a preferred embodiment, the stiffness, as measured by modified circular bending, is greater than about 400 grams. The stiffness of the protrusions 23 once again aids in maintaining separation between the lower surface 45 of the channels 21 and surfaces of the wearer's body that may be in contact with the protrusions 23.

Construction of Fluid Management Article

Figure 5:
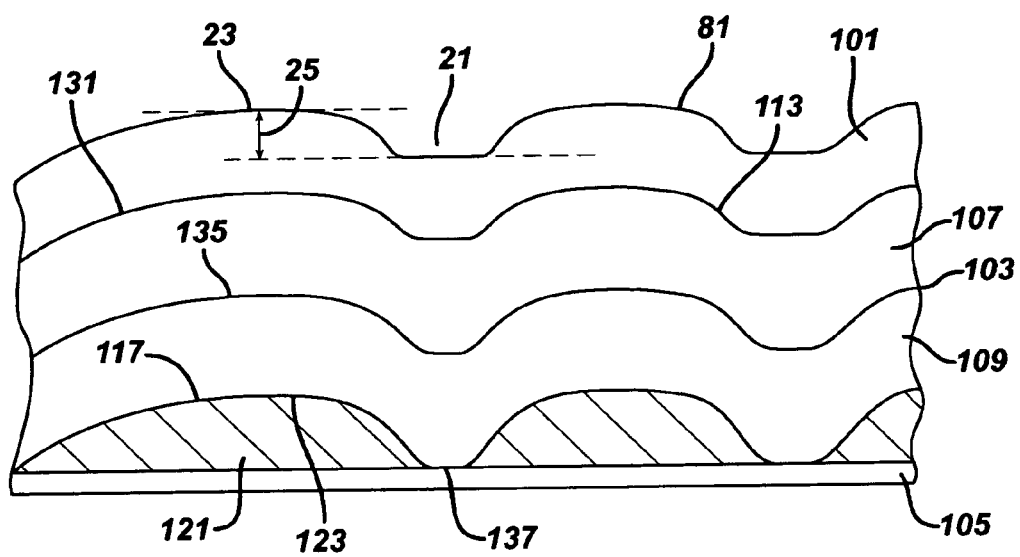
FIG. 5 is a fragmented, cross-sectional, close-up view of FIG. 3, showing additional features thereof.

Referring to FIG. 5, the sanitary napkin 1 comprises a fluid-permeable cover layer 101, a liquid-impervious barrier layer 105 and an absorbent system 103 intermediate the fluid-permeable cover layer 101 and the liquid-impervious barrier layer 105. As described previously, the sanitary napkin 1 comprises the plurality of fluid-guiding channels 21. The fluid-guiding channels 21 define therebetween the plurality of protrusions 23.

The cover layer 101 has a top surface that forms the top surface 81 of the sanitary napkin 1. The cover layer 101 is liquid permeable, and generally compliant, soft feeling, and non-irritating to the user's skin. It can be made from any of the materials conventional for this type of use. The cover layer 101 generally functions to transport fluid away from the wearer of the sanitary napkin 1 into the sanitary napkin 1. In this manner, fluid and moisture are removed from contacting the wearer, thus making the wearer feel dry and comfortable. Non-limiting examples of suitable materials that can be used as the cover layer 101 are woven and nonwoven fabrics formed from polyester, polypropylene, nylon, and/or rayon fibers or the topsheet may be an apertured thermo-plastic film and formed films. The cover layer 101 may optionally be treated with surfactant to manipulate the hydrophobicity/hydrophilicty thereof to facilitate optimal fluid transport properties. The fibers or other materials which make up the cover layer 101 should not collapse or lose their resiliency when subjected to body fluid. The cover layer 101 may be formed from, for example, staple fibers of polypropylene or other suitable materials. The fibers may be oriented by a carding process and thermally bonded via embossing. The basis weight of the cover layer 101 may range from about 10 grams per square meter (gsm) to about 30 gsm.

The barrier layer 105 is impervious to liquids and, thus, prevents bodily fluid that may be present at the interface between the absorbent system 103 and the barrier layer 105 from soiling the clothing of the user. Suitable materials that may be incorporated into the barrier layer 105 include, for example, embossed or non-embossed polyethylene films, microporous films, and laminated tissue, among other materials.

The absorbent system 103 provides the means for absorbing bodily fluid. Bodily fluid moving inward or "down" from the cover layer 101 is conveyed to the absorbent system 103 which retains the bulk of the fluid until the sanitary napkin 1 is discarded. The absorbent system 103 preferably comprises two separate layers, a transfer or acquisition layer 107 and an absorbent core 109. The transfer layer 107 and the absorbent core 109 may be discrete layers or may be unitized.

The transfer layer 107 is optional and, if present, is generally positioned directly underneath the cover layer 101, and the transfer layer 107 directly contacts the absorbent core 109. The transfer layer 107 provides the means of receiving body fluid from the fluid-pervious cover layer 101 and holding it until the absorbent core 109 has an opportunity to absorb it. The transfer layer 107 is, preferably, more dense than the fluid-pervious cover layer 101 and has a larger proportion of smaller pores than does the latter. These attributes allow the transfer layer 107 to contain body fluid and hold it away from the outer side of the fluid-pervious cover layer 101, thereby preventing the fluid from re-wetting the fluid-pervious cover layer 101 and its surface. However, the transfer layer 107 is preferably not so dense as to prevent the passage of the fluid through the transfer layer 107 and into the underlying absorbent core 109.

The transfer layer 107 may comprise various materials, including, for example, cellulose fibers such as from wood pulp, single component or bicomponent fibers that include thermoplastic materials (such as polyester, polypropylene, polyethylene, among others) in fiber or other forms, rayon, organic binders (such as copolymers of vinyl, acrylic and/or other monomers that may be coated onto thermoplastic fibers or otherwise incorporated into the transfer layer 107) among other materials known to the art. The transfer layer 107 may, for example, have a basis weight in a range from about 40 grams per square meter (gsm) to about 120 gsm, a thickness in a range from about 0.5 mm to about 4 mm, a density in a range from about 0.03 g/cc to about 0.15 g/cc. For embodiments in which the protrusions 23 and the channels 21 are formed through the transfer layer 107 it is preferred that the transfer layer 107 have a melt-processible or thermoplastic component such as polyethylene, polypropylene, polyester, and the like. The transfer layer 107 may be moldable or compressible or otherwise assist in maintaining the definition of the plurality of protrusions 23 and the plurality of channels 21 during the wearing of the sanitary napkin 1.

The absorbent core 109, positioned underneath the optional transfer layer 107, has a high capacity for absorbing liquids and may be capable of maintaining the definition of the plurality of protrusions 23 and the plurality of channels 21 during the wearing of the sanitary napkin 1. Examples of material that may be used in the construction of the absorbent core 109 include, for example, cellulosic fibers (preferably wood pulp, but cotton, flax and peat moss are acceptable), synthetic fibers, superabsorbent polymers (SAP) or superabsorbent fibers, as well organic binders or other materials described above as suitable for incorporation into the transfer layer 107, and other materials known to the art of manufacturing absorbent core materials. The relative proportion of these materials may be varied to achieve sufficient absorbency, compressibility, and processibility. In one non-limiting example, the absorbent core 109 comprises from about 40 weight percent to about 95 weight percent cellulosic fibers, and from about 5 weight percent to about 60 weight percent superabsorbent polymer.

The absorbent core 109 may include any superabsorbent polymer (SAP). For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and other material known to the art of absorbent article manufacture.

The absorbent core 109 may be resin or thermal bonded, and flat or emboss calendared to achieve an appropriate strength. The density of the absorbent core 109 is preferably in a range from about 0.08 g/cc to about 0.60 g/cc, and more preferably in a range from about 0.20 g/cc and about 0.40 g/cc. The basis weight of the absorbent core 109 is preferably in a range from about 100 gsm to about 350 gsm, and more preferably between about 150 gsm and about 250 gsm.

While the various material layers (cover, absorbent system, barrier) are described as separate layers, it is within the scope of the invention that one or more of these layers may be formed or integrated together and may actually not be discrete material layers, but rather a unitary layer possessing multiple functional properties.

Referring again to FIG. 5, the protrusions 23 and the channels 21 of the sanitary napkin 1 are formed through the top surface 81 (i.e., the top surface of the cover layer 101). By "formed through the top surface of the cover layer" it is meant that if one were to follow the top surface 81 of the sanitary napkin 1 (i.e., the top surface of the cover layer 101), one would observe the undulations of the protrusions 23 and channels 21. In other words, the cover layer 101 is not loosely draped over underlying material layers so as to mask or mute the protrusions 23 and the channels 21 to the extent that the protrusions 23 and channels 21 lose definition.

The protrusions 23 and channels 21 preferably extend into additional material layers of the sanitary napkin 1, as described below. In the embodiment of the invention shown in FIG. 5, the protrusions 23 and channels 21 are formed through the cover layer 101, the transfer layer 107 and the absorbent core 109. By "formed through," the transfer layer 107 and the absorbent core 109, it is meant that if one were to follow a top surface 131 of the transfer layer 107, one would find a plurality of protrusions and channels that correspond, register, with or align with the protrusions 23 and channels 21 in the top surface 81 of the cover layer 101. As such, the cover layer 101 fits snugly over the transfer layer 107, and the top surface 131 of the transfer layer 107 generally follows the contours in the top surface 81 of the cover layer 101 with no appreciable macroscopic voids present between the two layers. Similarly, a top surface 135 of the absorbent core 109 follows the contour of the top surface 131 of the transfer layer 107. While it is preferred that the protrusions 23 and the channels 21 are formed through the transfer layer 107 and through the absorbent core 109, this is not required. For example, the protrusions may be formed through only one of these layers and/or formed through, for example, an insert (not shown in the Figures) that has no absorbent functionality and is positioned between the cover layer 101 and the barrier layer 105.

The shape of the protrusions and channels that are present in the top surfaces 131, 135 of the transfer layer 107 and absorbent core 109 respectively may differ from the corresponding protrusions 23 and channels 21 in the top surface 81 of the cover layer 101. Similarly, the protrusions in the top surfaces 131, 135 of the transfer layer 107 and the absorbent core 109 respectively, may be more or less pronounced than the corresponding protrusions 23 and channels 21 in the top surface 81 of the cover layer 101.

While it is contemplated that the plurality of protrusions 23 and the plurality channels 21 may be formed through the barrier layer 105, it is preferred that they are not. In this preferred embodiment, portions 117 of the absorbent system 103 are detached from the barrier layer 105 and portions 137 contact the barrier layer 105. The portions 117 of the absorbent system 103 that are detached from the barrier layer 105 may have a density that is less than a density of the portions 137 that contact the barrier layer 105. In this embodiment of the invention, a plurality of voids 121 are present in between the barrier layer 105 and the detached portions 117 of the absorbent system 103. As such, a plurality of recesses 123 are present in the underside of the absorbent system 103. This plurality of recesses 123 are generally aligned or in registration with the plurality of protrusions 23.

Referring again to FIG. 1a, the absorbent system 103 may be confined to a laterally central region of the sanitary napkin 1. Alternatively, the absorbent system 103 may extend laterally into the flap 13. As shown in FIGS. 1 and 2, the cover layer 101 and the barrier layer 105 are joined at a seam 40 (also commonly referred to as a flange seal), around the entire periphery of the sanitary napkin 1. The purpose of this seam 40 is to unite the cover layer 101, barrier layer 105, and the absorbent system 103 of the sanitary napkin 1 into a unitary structure. The seam 40 can be formed by any means commonly used in the art for this purpose such as by gluing, crimping, or heat-sealing. The seam 40 is illustrated extending completely around the periphery of sanitary napkin 1. Additional securement of the layers 101, 103, 107, 109 may be achieved by laminating one or more of these layers together.

Method of Making the Fluid Management Article

The fluid management article of the present invention such as the sanitary napkin 1 may be made using various processes, such as, for example, an embossing process in which one or more material layers of the sanitary napkin 1 are subject to mechanical and thermal energy to form the protrusions 23 and the channels 21.

In accordance with one aspect of the invention, a method of making a fluid management article such as the sanitary napkin 1 comprises providing a body-faceable, liquid-pervious cover layer having a top surface, a garment-faceable, liquid-impervious barrier layer, and an absorbent system. The absorbent system is positioned intermediate the body-faceable, liquid-pervious cover and the garment-faceable, liquid-impervious barrier. A plurality of fluid-guiding channels, the fluid-guiding channels defining therebetween a plurality of protrusions, are formed through the top surface of the cover layer. The protrusions have an apex that extends a height that is greater than about 0.5 mm above at least a portion of the plurality of channels. The absorbent system may be positioned intermediate the body-faceable, liquid-pervious cover and the garment-faceable, liquid-impervious barrier prior to forming the channels and protrusions through the top surface of the cover layer. Alternatively, the absorbent system may be positioned intermediate the body-faceable, liquid-pervious cover and the garment-faceable, liquid-impervious barrier after forming the channels and protrusions through the top surface of the cover layer.

In accordance with another aspect of the invention, a method of making a fluid management article such as the sanitary napkin 1 comprises forming a plurality of fluid-guiding channels, the fluid-guiding channels defining therebetween a plurality of protrusions, wherein the plurality of fluid-guiding channels and the plurality of protrusions are formed through the top surface of the cover layer. The forming includes urging a first material layer between a two rollers, wherein one of the rollers includes a plurality of projections and the other roller includes a plurality of depressions in registration with the projections of the first roller, and wherein the first material layer is selected from the group consisting of the body-faceable, liquid-pervious cover the absorbent system, a mechanical insert, and combinations thereof.

Figure 6:
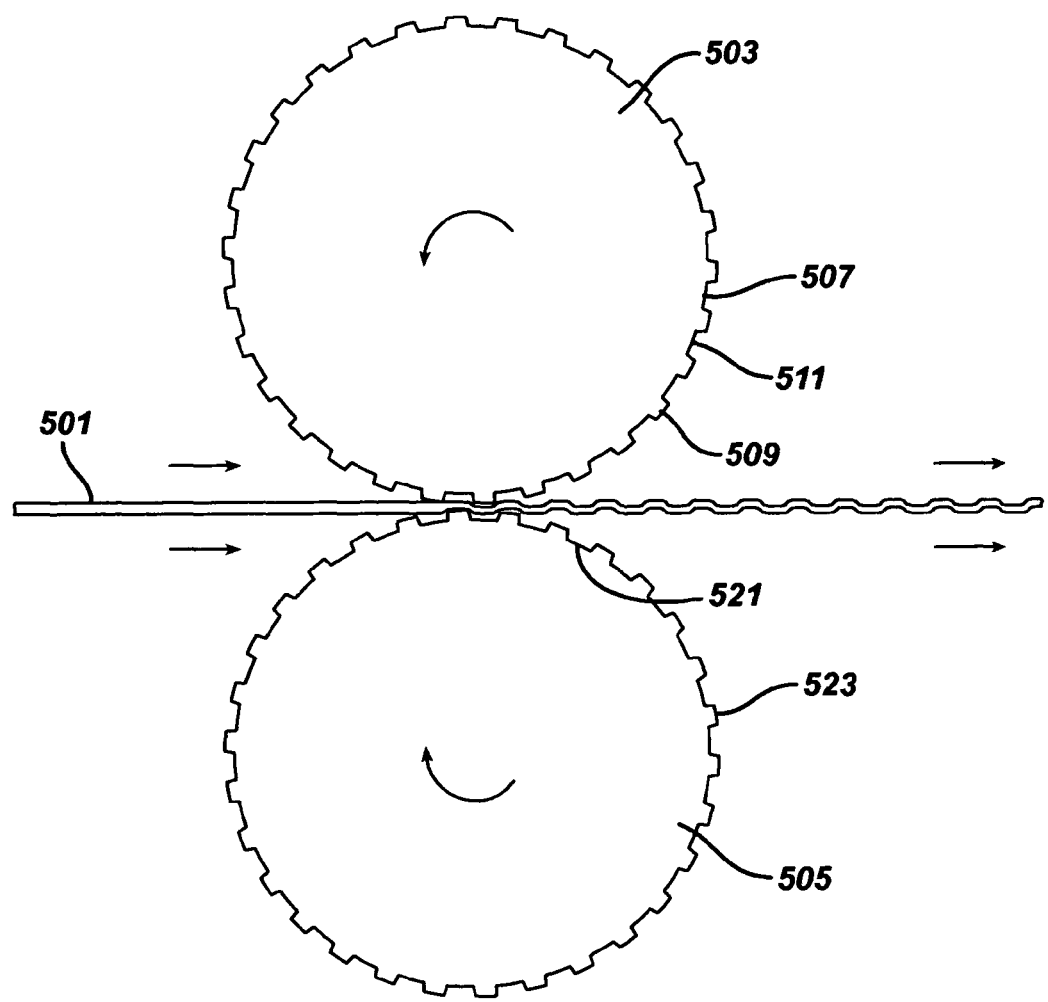
FIG. 6 is a cross-sectional view of a web being urged between two rollers, consistent with embodiments of the inventions described herein.

Referring to FIGS. 1, 5, and 6 in one exemplary method consistent with embodiments of the present invention, the absorbent core 109 and the transfer layer 107 may be formed by cutting respective webs of material to pre-determined sizes and shapes, placing the cut absorbent core 109 and the transfer layer 107 in contact with one another, and providing the absorbent core 109 and the transfer layer 107 to a conveyer. A web of material that will eventually be trimmed to create the cover layer 101 may then be provided such that the web of cover material contacts the transfer layer 107, forming a layered web 501, as shown in FIG. 6. This layered web 501 is then urged between a rotating die roller 503 and a rotating anvil roller 505 that is spaced apart from the die roller 503. The die roller 503 has a surface 507 with a pattern of projections 509 (i.e., male tooling elements) extending from a generally flat surface. The anvil roller 505 has a surface 523 that may be substantially flat in its entirety. However, in a preferred embodiment, the surface 523 of the anvil roller 505 includes a series of depressions 521 (female tooling elements) that are designed to align with the projections 509 of the die roller 503.

As the web 501 is urged between the die roller 503 and the anvil roller 505, the web 501 is subjected to periodic compression/shearing forces. The web 501 is thereby deformed and a pattern of protrusions 23 and channels 21 is formed in the web 501. The protrusions 23 and channels 21 have dimensions that are related to those of the projections 509 and the depressions 521 in the die roller 503 and the anvil roller 505 respectively.

Figure 7:
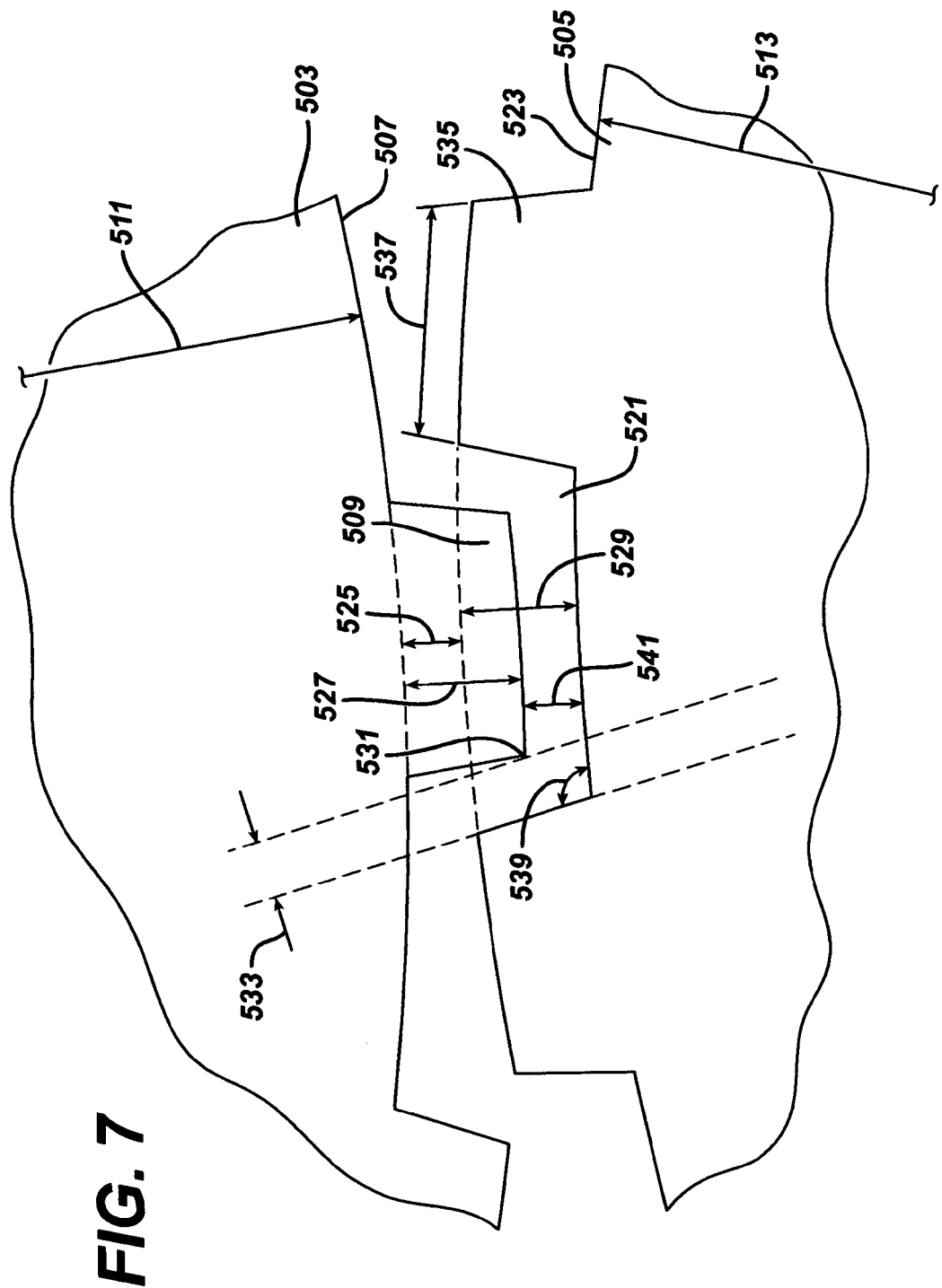
FIG. 7 is a dose-up, cross-sectional view of the rollers of FIG. 6.

FIG. 7 shows a close-up view of the rollers 503, 505 of FIG. 6. The die roller 503 and the anvil roller 505 are spaced apart by a tool gap 525 that is preferably maintained within a narrow range throughout the processing of the web 501. The tool gap 525 may be maintained (within a few hundredths of a mm) about a target that may be between about 0.2 mm to about 0.3 mm.

The projections 509 of the die roller 503 have a projection height 527 that is selected based upon the desired heights 25 of the protrusions 23. The projection height 527 may, for example, be between about 1 mm and about 3 mm.

The projections 509 may be rounded to form rounded (e.g. mesa shaped) protrusions 23, thereby providing a pleasing sensory experience for the user, but this is not required. In one embodiment of the invention, the projections 509 have an individual radius 531 that may be between about 0.25 mm and about 1 mm.

The depressions 521 have a depth 529. A top clearance 541 separates the projections 509 from a bottom of the depressions 521, such that the sum of the projection height 527 plus the top clearance 541 is equal to the tool gap 525 plus the depression depth 529. The top clearance 541 may be greater than the caliper 26 of the sanitary napkin 1. By having depression depths 529 that meet this criteria, compression of the sanitary napkin 1 in the regions that will form the protrusions 23 is relatively low. This facilitates the formation of protrusions 23 with reasonable large heights 25 and, as such, fluid management articles with better absorbency properties.

A side clearance 533 is present between the projections 509 and the depressions 521. The side clearance 533 is substantially less than the caliper 26 of the sanitary napkin 1. As such, the maximum compression is between the projection 509 and the lands 535, not directly underneath the projection 509. The side clearance 533 may be in a range from about 0.5 mm and about 1.5 mm. Furthermore, the die roller 503 has a pitch diameter 511 that is preferably approximately the same as a pitch diameter 513 of the anvil roller 505.

The depressions 521 are separated by lands 535 having a land width 537. The land width 537 is generally selected based upon the desired pattern imparted to the sanitary napkin 1, and, in particular, the width 56 of the channels 21. The land width may be, for example, between about 1 mm and about 2 mm. The lands have an angle 539 that is generally selected to facilitate removal of debris that may accumulate during processing from the die roller 503. The angle may be between about 0 degrees and about 15 degrees.

The projections 509 and the depressions 521 are each maintained at a surface temperature that enhances the ability of the web 501 to maintain the pattern of protrusions 23 and the channels 21 as well as to permit the web 501 to accept the pattern at a line speed that is relatively fast. The surface temperature may be in a range from about 100 degrees Celsius to about 200 degrees Celsius, and may be sufficiently high to promote localized melting and fusing of the various materials that comprise the web 501. The projections 509 and the depressions 521 may be maintained at surface temperatures that are approximately the same or substantially different.

The die roller 503 and the anvil roller 505 are preferably constructed from durable materials that are capable of being heated to a temperature greater than about 200 C. The die roller 503 and the anvil roller 505 may comprise, for example, stainless steel, elastomeric materials, or other materials known to the art of the embossing of materials used in absorbent article manufacture.

The web 501 is advanced between the rollers 503, 505 at a surface speed that may be from about 5% to about 25% greater than a speed associated with the rollers 503, 505. This is typically necessary in order to generate protrusions 23 having height 25 greater than about 0.5 mm. Stated in other words, the compression and deformation associated with the web 501 generally requires greater material consumption than for processing that does not impart substantial height to the web 501.

The web 501 includes a material that is capable of being durably deformed, i.e., capable of retaining a pattern imparted to the web 501 by the projections 509 and depressions 521. The web 501 comprises one or more materials that have sufficient stiffness, moldability, and/or compression resistance such that the web 501 can accept a pattern such as from patterned rollers 503, 505, thereby forming the protrusions 23 and the channels 2,1 and the sanitary napkin 1 retains this pattern throughout the period during which the sanitary napkin 1 is used.

In a preferred embodiment of the invention, the web 501 includes at least a portion of the absorbent system 103. The absorbent system 103 may comprise an absorbent core 109 and a transfer layer 107, or the web 501 may comprise only the absorbent core 109. The web 501 may further comprise the cover layer 101. Although it is preferred that the web 501 does not include the barrier layer 105 (the process may damage the barrier layer 105), including the barrier layer 105 in the web 501 is contemplated. The web 501 is urged between the die roller 503 and the anvil roller 505 and the plurality of protrusions and channels are formed through the absorbent system 103 as well as other material layers that may be included in the web 501.

Figure 8:
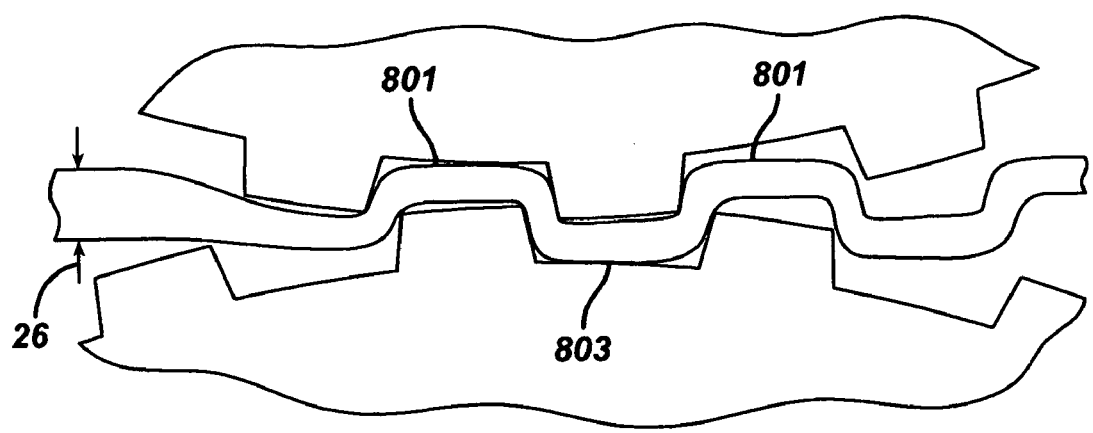
FIG. 8 is the close-up, cross-sectional view of the web of FIG. 7, depicting the web being deformed by said rollers.

As shown in FIG. 8, the sanitary napkin 1 is subjected to high compression forces in a region 801 that generally encompasses the channels 21. As such, regions 801 are highly densified. Regions 803 (generally encompassing the protrusions 23) are subject to only minimal compression because the depression depth 529 is generally larger than the sum of the caliper 26 of the sanitary napkin 1 plus the projection height 527. As such regions 803 are relatively undensified and lofted. Regions 805 (generally encompassing the edge 57 of the protrusions 23) are subject to moderate shear and compression from the process because the caliper 26 of the sanitary napkin 1 is less than the side clearance 533. As such, the regions 805 are partially densified.

Thereafter, the sanitary napkin 1 manufacturing process is completed using process steps known to the art of sanitary napkin manufacture. For example, for the embodiment of the invention in which the web 501 excludes the barrier layer 105, the barrier layer 105 may be brought into contact with the absorbent system 103 and adhered thereto using suitable construction adhesive to form a bond. In one embodiment of the invention, the barrier layer 105 is adhered to the portions 137 of the absorbent system 103 and not to detached portions 123 of the barrier layer 105 (as shown in FIG. 5). Release paper and positioning adhesive may be applied to the barrier layer 105 using methods known to the art of sanitary napkin manufacture. The footprint boundary 2 may be formed by, for example, by forming the flange seal 40 using heated embossing rollers and using a die roller having cutting blades in order to cut the desired shape into the various material layers comprising the sanitary napkin 1.

Procedure for Determining Height and Width of Protrusions

Height and width of protrusions may be determined using mechanical measurement systems known to the art, but for accurate measurements it is preferred that an optical measurement system is employed. For example, one particular method that is capable of accurately determining height and width of the protrusions 23 involves the use of a digital stripe protrusion technique, such as the PRIMOS optical 3D skin measurement system, commercially available from GFMesstechnik GmbH of Berlin, Germany. Although the PRIMOS optical 3D skin measurement system is generally used for taking in vivo skin measurements, it can also be used to take 3D surface measurements of inanimate objects, such as fluid management articles including sanitary napkins.

Figure 9:
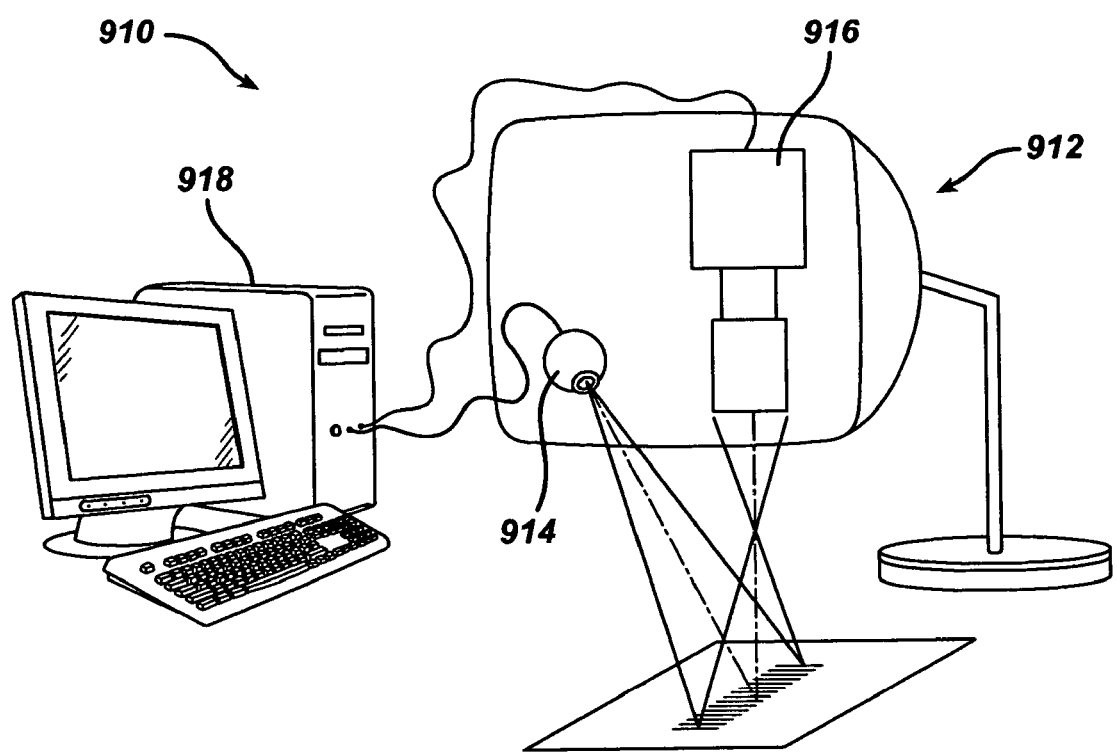
FIG. 9 is a schematic diagram of an optical measuring system that may be used to characterize fluid management articles of the present invention.

Shown in FIG. 9, is a schematic representation of an optical 3D measurement system 910 that is suitable for obtaining 3D surface measurements of the fluid management article, such as the sanitary napkin 1 of the present invention. The optical 3D measurement system 910 includes an optical measurement head 912 having a light projector 914, a CCD recording camera 916 and a protrusion and shooting optic (not shown). The light projector 914 may be a digital micromirror projector such as a Digital Micromirror Device (DMD) that is available from Texas Instruments of Houston, Tex. In operation, the light projector 914 projects a series of alternating black and white parallel stripe patterns onto the surface of the sanitary napkin, wherein each stripe pattern has stripes of different widths. The minute elevation differences on the surface of the sanitary napkin 1 distort the parallel stripes, and it is these distortions that constitute a qualitative and quantitative representation of the surface profile of the sanitary napkin 1.

The CCD recording camera 916 acquires the pictures of the distorted stripe patterns and forwards them to a processing unit 918, such as a personal computer, that is connected to the optical measurement head 912. The processing unit 918 is operative to drive the light projector 914 and receive signals from the CCD recording camera 916. The pictures acquired by the CCD recording camera 916 and received by the processing unit 918 are analyzed by the processing unit 918 in order to derive surface measurements of the sanitary napkins being measured. The processing unit 918 may employ PRIMUS SOFT software, also commercially available from GFMesstechnik of Berlin, Germany, in order to interpret the data from the CCD recording camera 916.

One suitable process for obtaining height measurements using the PRIMOS optical 3D measurement system 910, is as follows. Firstly, the optical 3D measurement system 910, the light projector 914, a CCD recording camera 916, and the processing unit 918 are powered and allowed to warm up. Once warmed up, the "technical surface" setting is selected, which is the appropriate setting for obtaining surface measurements of inanimate objects. The next step is to perform a calibration procedure. For example, in order to calibrate the PRIMOS optical 3D measurement system 910, a calibration block having a trench of a certain vertical depth is placed on a level table under the optical measurement head 912 and the focus and light intensity of the equipment are adjusted. In order to adjust the light intensity, a light adjustment knob located on the camera is manually adjusted until a visual indicator in the form of a circle that changes color, turns green. The green circle indicates that the light intensity is properly set. The focus is adjusted by adjusting a red-screen cross hair such that it is in alignment with a black cross hair.

Once the light intensity and focus have been set, the user hits the "measure" button. The "measure" button causes the PRIMUS SOFT program to generate an index color image of the reference block's surface, which is shown to a user on a display screen. The index color image shows the object's surface in different colors depending on the surface's different vertical heights. A profile line is drawn perpendicular to the reference block's trench on the display screen using a mouse or other suitable user interface. The PRIMUS software then generates a two dimensional graph of the reference block's surface profile along that profile line. In order to determine the height of the trench, the mouse is clicked on the two dimensional graph at a location that represents the top surface of the reference block. The mouse is then clicked a second time on the two dimensional graph at a location that appears to be the bottom of the trench. The user then selects a vertical distance function from a tool bar or from a drop down menu. The vertical distance function provides the vertical distance between the two locations on the profile where the mouse was clicked. That vertical distance is then compared to the reference distance indicated on the reference block. If the measured distance is within 1% of the distance indicated on the reference block, then the PRIMUS optical 3D measurement system 910 is calibrated.

Once calibrated, the reference block is removed, and the sanitary napkin 1 is secured in a flattened manner on the table with no material layers of the sanitary napkin 1 removed. The sanitary napkin 1 is placed under the optical measurement head 912. The light intensity and focus are adjusted once more and the "measure" button is selected. The PRIMUS SOFT program generates an index color image of the sample being measured. A profile line is then drawn on the index color image perpendicular to the region where the height measurement is going to be taken. A two dimensional graph of the sample's surface profile along that profile line is then generated. Once generated, the mouse is clicked on the two dimensional profile at a location that most closely approximates an imaginary reference plane that is coincident with the lower surface 45 of the channel 21 (and parallel to plane 49, described with reference to FIG. 3) that is adjacent to (i.e., isolates) the projection 23. The mouse is then clicked a second time at a location on the two dimensional graph that most closely approximates the top of a protrusion. The user then selects the vertical distance function, which provides the vertical distance between the two locations on the profile where the mouse was clicked, which in the case of the present invention would be the height of the protrusion.

The individual width 55 of protrusions 23 are generally calculated as the projected area of the protrusion 23 divided by a length of the protrusion, wherein the length is greatest distance between any two points on the protrusion, as measured using the optical measurement system 910. For a description of a suitable method of determining the width of a protrusion, the reader is directed to patent application, "Thin Sanitary Napkin Having Body-Faceable Protrusions," incorporated by reference, as stated previously.

To facilitate obtaining accurate measurements of height and width, the optical measurement head 912 may use, for example, a 32 mm×32 mm field of view, with an x-y spatial resolution of 32 microns and a z-step resolution of 1 micron in order to obtain surface measurements of the sanitary napkin of the present invention. In addition, the point cloud from each acquisition may, for example, have 1,048,576 points (1024×1024).

Procedure for Determining Penetration Time

The "penetration time" is defined as the time taken for the napkin 1 to absorb a predetermined quantity of a specific liquid in accordance with the test procedure described in detail below. The inventors have found that fluid management articles consistent with embodiments of the invention described hererin, advantageously provide low penetration times.

The apparatus required for the test includes a stop watch with an accuracy to 0.1 sec, a graduated glass cylinder of 10 ml capacity and having an internal diameter of approximately 12 mm, a quantity of synthetic menstrual fluid, and a fluid penetration test orifice plate. The test plate is rectangular and made from polycarbonate and is 25.4 cm (10.0 inches) long by 7.6 cm (3.0 inches) wide by 1.27 cm (0.5 inches) thick. A concentric, elliptical orifice is formed through the plate having a major axis of length 3.8 cm and being parallel to the length of the plate and a minor axis of width 1.9 cm and being parallel to the width of the plate.

The apparatus further includes a resilient cushion for supporting the sanitary napkin 1 during the penetration time test and which acts to improve the contact between the plate and cover layer 101. The cushion comprises a fusible fiber non-woven fabric of low density (0.03 to 0.5 g/cm.sup.3) measured at 0.24 kPa (0.35 psi). The non-woven fabric is cut into rectangular sheets of dimensions 32.×14.×0.3 centimeters and the sheets are stacked until the stack reaches a free height of about 5 cm. The stack is then wrapped with one layer of 0.1 mm (0.004 inch) thick polyurethane elastomeric film such as BF Goodrich's Tuftane. The film wrap is sealed on the back with double-face clear tape to form a resilient cushion. This resilient cushion should respond to a load formation such as when using the Fraser Compressometer No. 255 equipped with the 12.7 cm (5 inch) diameter foot, the thickness of the cushion varying in the following way:

| Applied Pressure | Thickness (after being wrapped with film) |
| --- | --- |
| 0 pressure | 42.0 mm |
| 0.069 kPa (0.70 g/cm2; 0.01 psi) | 38.5 mm |
| 0.207 kPa (2.1 g/cm2; 0.03 psi) | 31.0 mm |
| 0.345 kPa (3.52 g/cm2; 0.05 psi) | 27.0 mm |
| 0.483 kPa (4.9 g/cm2; 0.07 psi) | 24.0 mm |

The sanitary absorbent napkin 1 (with any packaging removed), the test fluid, the orifice plate and the graduated cylinders are conditioned at a temperature 21+/−1 degrees C. and 50.+/−0.2% relative humidity (RH) for a minimum of 8 hours prior to testing. If the napkin 1 is folded, the creases are removed as far possible by flattening and if the napkin 1 is curved, the side gathers are cut through several times so that the sample can be flattened.

The preconditioned sanitary napkin 1 is placed on the resilient cushion on a level surface, without removing the release paper and with the cover layer 101 facing upwards.

The cleaned orifice plate is placed on the sample, with the orifice centered on the napkin's surface so that the major axis of the elliptical orifice is coincident with the longitudinal axis of the napkin 1. If the napkin 1 has at least one channel, the plate should be positioned so that at least one channel lies within the orifice or adjacent the edge of the orifice. The graduated cylinder is then filled with 7 ml of synthetic menstrual test fluid. Suitable synthetic menstrual fluid has a viscosity of 30 centipoise (cps).

Holding the spout of the graduated cylinder approximately 1 to 3 inches above the orifice plate, the test fluid is poured into the orifice and the stop watch is started when the fluid first touches the sample. The stop watch is stopped when the cover layer 101 first appears through the top surface of the fluid, regardless of where the cover layer 101 becomes visible within the orifice. The time is measured to the nearest 0.1 seconds. The fluid should be poured into the orifice in such a manner that the orifice is kept as full as possible without overflowing onto the face of the plate.

When conducting the above method, it is important that the tests are performed at a temperature of 21.+−0.1.degree. C. and 50.+−0.2% relative humidity. It is also important that the samples, all components of the apparatus and the test fluid are conditioned for a minimum of eight hours at the conditions specified above prior to testing. The orifice plate should be thoroughly cleaned between test samples. Also, the test fluid container should not be left uncovered between testing of each sample as the evaporative effects will alter the fluid. It is also important that the correct end point is used when timing fluid penetration. If any of the above conditions are not met, the test results can be adversely affected.

This test is performed on a minimum of 5 samples and an average value of the 5 samples is reported as the penetration time.

Procedure for Determining Re-Wet

A standard quantity of test fluid is deposited on the surface of a sanitary napkin and allowed time to absorb. The wetted area is then covered with an absorbent medium, placed under a specific pressure for a specific time period and then removed.

Rewet potential of the napkin is determined by measuring the amount of fluid absorbed by the absorbent medium placed on the wetted area. The apparatus includes a stopwatch, capable of 1.0 sec. accuracy and 15 min. duration; a balance, 50 g minimum capacity and 0.01 g accuracy, a balance, 3 Kg minimum capacity and 0.1 g accuracy; a ½" thick PLEXIGLAS Orifice Plate , a ½" thick PLEXIGLAS Support Plate; an accurate fluid dispensing device (preferred is a disposable syringe, such as, B-D 20 cc syringe or Lancer 12 cc pipet, but a graduated cylinder, appropriately sized for accurate measurement of 5 cc of fluid is adequate; Whatman #1 qualitative filter paper (46 cm×57 cm, 100 sheets/pkg.); a wide mouth plastic bottle with lid. Bottle diameter: 3" or less having a capacity: 500 ml to 1000 ml range; paper towels; a water supply for cleaning apparatus; and a cuttingboard or 3"×4" steel rule die.

The sanitary absorbent napkin 1 (with any packaging removed), the test fluid, the PLEXIGLAS plates, fluid dispensing device and filter paper are conditioned at a temperature 21.+/−1 degree C. and 50.+−.2% relative humidity (RH) for a minimum of 8 hours prior to testing. If the napkin 1 is folded, the creases are removed as far possible by flattening and if the napkin 1 is curved, the side gathers are cut through several times so that the sample can be flattened.

The preconditioned sanitary napkin 1 is placed on a level surface, without removing the release paper and with the cover layer 101 facing upwards.

The cleaned orifice plate is placed on the sample, with the orifice centered on the napkin's surface so that the major axis of the elliptical orifice is coincident with the longitudinal axis of the napkin 1. If the napkin 1 has at least one channel, the plate should be positioned so that at least one channel lies within the orifice or adjacent the edge of the orifice. The fluid dispensing device is then filled with 5 ml of synthetic menstrual test fluid. Suitable synthetic menstrual fluid has a viscosity of 30 centipoise (cps).

Holding the fluid dispensing device approximately 1 to 3 inches above the orifice plate. The fluid should be dispensed into the orifice in such a manner that the orifice is kept as full as possible without overflowing onto the face of the plate. After absorption is complete start stopwatch and remove the PLEXIGLAS orifice plate.

After 15 minutes has elapsed on the stopwatch, quickly stack on the wetted area, in the following order:

1. 15 ply (pre-weighted) stack of 3"×4" Whatman #1 filter paper (4" length coincident with the longitudinal length of the napkin)

2. Plexiglas support plate (centered over filter paper)

3. Plastic container of predetermined amount of steel shot (centered on PLEXIGLAS support plate). The weight of shot in grams should be about [0.6 lb/sq.in.×contact area in sq.in.× 453.6 g/lb] minus [the combined weight of the filter paper, the support plate, the bottle and the lid].

Note, to calculate the contact area of Rectangular Pads, area=4"×Napkin Width. To calculate contact area of raised center or pads; saturate a piece of 3"×4" filter paper with the test fluid. In the following order, place the wet filter paper, "×4" support plate and bottle with 3 Kg of steel shot onto the center of the napkin face. After 10 to 15 sec. has elapsed, remove all of the above from the napkin. A stain, equivalent to the contact area of the filter paper with the napkin, should be apparent on the napkin face. Measure the stain area using the Planimax 25 Image Analyser or trace the stain onto a thin PLEXIGLAS plate or transparent MYLAR sheet and measure the stain area with a planimeter. NOTE: use an average value for the weight of the filter paper stacks. Weigh out the calculated amount of shot, place into the plastic bottle and secure the lid.

Immediately after placing the above components on the napkin, start the stopwatch. When 3 minutes has elapsed on stopwatch, remove the plastic container and support plate. Weigh and record the wet weight of the 15 ply filter paper stack to 0.01 g.

Note that the orifice plate should be thoroughly cleaned between test samples. Also, the test fluid container should not be left uncovered between testing of each sample as the evaporative effects will alter the fluid. It is also important that the correct end point is used when timing fluid penetration. If any of the above conditions are not met, the test results can be adversely affected.

This test is performed on a minimum of 5 samples and an average value of the 5 samples is reported as rewet.

Procedures for Determining Stiffness

Peak bending stiffness is determined by a test that is modeled after the ASTM D 4032-82 CIRCULAR BEND PROCEDURE, the procedure being considerably modified. Test specimens are conditioned by leaving them in a room that is 21° C., +/−0.1° C. and 50%, +/−2.0%, relative humidity for a period of two hours. The plunger speed is set at 50.0 cm per minute per full stroke length. A specimen is positioned such that the continuous region 27 of protrusions 23 and channels 21 are on the orifice platform below the plunger. The body-facing layer of the specimen is facing the plunger and the barrier layer of the specimen is facing the platform. The indicator zero is checked and adjusted, if necessary. The plunger is actuated. Touching the specimen during the testing should be avoided. The maximum force reading to the nearest gram is recorded. The above steps are repeated until all of the specimens have been tested. The method is otherwise performed as described in U.S. Pat. No. 5,009,653, issued to the Procter & Gamble Company of Cincinnati, Ohio on Apr. 23, 1991, which is incorporated herein by reference.

EXAMPLES

Example 1

A thin sanitary napkin comprising a 30 gsm cover layer, a 100 gsm transfer layer and a 208 gsm absorbent core and a barrier layer was constructed. A plurality of channels and protrusions similar to those described in FIG. 1a, were formed through the cover layer, the transfer layer, and the absorbent core, but not the barrier layer. The height of the protrusions was about 1 mm. The protrusions were alternating narrow and long rectangles, as described above with reference to FIG. 1a and were present in a number density of about 2 protrusions per square centimeter.

The sanitary napkin was tested according to the test methods described above and was found to have a penetration time of 24.5 seconds and a rewet value of 0.74 seconds.

Example 2

A sanitary napkin comprising a 30 gsm cover layer, a 110 gsm transfer layer and a 208 gsm absorbent core and a barrier layer was constructed. A plurality of channels and protrusions similar to those described in FIG. 1a, were formed through the cover layer, the transfer layer, and the absorbent core, but not the barrier layer. The height of the protrusions was about 2 mm. The protrusions were present in a number density of about 2 protrusions per square centimeter. The sanitary napkin was tested according to the test methods described above and was found to have a penetration time of 19.6 seconds and a rewet value of 0.64 seconds.

Comparative 1

A sample "Stay-Free Ultra Thin Maxi," commercially available from Johnson & Johnson Consumer Companies, Inc. The sanitary napkin was tested according to the test methods described above and was found to have a penetration time of 29 seconds and a rewet value of 0.95 seconds.

Method of Using the Fluid Management Article

The fluid management article of the present invention is placed in proximity to or in contact with the wearer's body, with the protrusions 21 positioned towards the body with respect to the wearer. For example, for the case of the sanitary napkin 1, the sanitary napkin 1 is placed in the crotch portion of an undergarment and positioned in proximity to the wearer's perineal region in order to manage fluids emanating therefrom. The sanitary napkin 1 may be secured to a wearer's undergarment in order to remain close to the vaginal opening using positioning adhesive. The protrusions 23 are generally capable of maintaining a separation between the lower surface 45 of the channels 21 and a surface of the wearer's body that may contact the protrusions 23 during use.

Fluid emanating from the wearer is transmitted through the cover layer 101 and into the absorbent system 103 where the fluid is primarily housed until the absorbent article is then discarded. Without wishing to be bound by a specific theory or mechanism of action, the sanitary napkin 1 of the present invention is believed to demonstrate superior absorbency performance in that fluid impinging upon the protrusions of the sanitary napkin 1 may be partially directed downward into the absorbent structure and partially directed from the protrusions 23 into the channels 21. This allows fluid, even relatively viscous fluid and fluid with high solids content to penetrate the sanitary napkin 1 and be rapidly directed away from the wearer, thereby improving the wearer's comfort. Furthermore, it is believed that because the protrusions have a height that is greater than prior art protrusions, the protrusions generally express less fluid in re-wet challenge, thereby preventing product leakage and enhancing comfort. Enhanced re-wet may be further strengthened for embodiments in which the sanitary napkin 1 has partially densified region 805 associated with the protrusions, possibly because the partially densified regions 805 of the protrusions hold fluid better in re-wet challenge than would protrusions made using prior art processes.

The fluid management article of the present invention are advantageous in that they are characterized as having low penetration time required to absorb fluid, even viscous fluid such as blood and menses. In addition, fluid that is absorbed by the article is held within the structure and not released when the article is exposed to compression and other forms of mechanical deformation. Furthermore, the protrusions are generally soft and comfortable to the wearer.

While the foregoing is directed to various embodiments of the invention, other and further embodiments may be devised without departing from the basic scope thereof, and the scope thereof is determined by the claims that follow:

What is claimed is:

1. A fluid-management article, comprising:
   a body-faceable, liquid-pervious cover having a top surface;
   a garment-faceable, liquid-impervious barrier; and
   an absorbent system intermediate the cover and the barrier, wherein the fluid-management article comprises a plurality of fluid-guiding channels, wherein the fluid-guiding channels entirely surround each one of a plurality of isolated protrusions, wherein the channels and the protrusions are formed through the top surface of the cover and at least a portion of the absorbent system, wherein the protrusions have an apex that extends a height above at least a portion of the plurality of channels, wherein the height is greater than about 0.5 millimeters (mm), and wherein the protrusions have a number density greater than about 0.15 protrusions/cm$^2$.

2. The fluid management article of claim 1 wherein the protrusions have a sufficient resilience, when wet, of maintaining a separation between the channels and a surface of the wearer's body, when the fluid management article is worn by a user.

3. The fluid management article of claim 1 wherein the protrusions and the channels form a continuous region.

4. The fluid management article of claim 3 wherein the continuous region extends across a centerline of the article, wherein the centerline is selected from the group consisting of the longitudinally-extending centerline, the transversely extending centerline and combinations thereof.

5. The fluid-management article of claim 1 wherein the channels form a continuous interconnected network that defines at least two adjacent protrusions.

6. The fluid management article of claim 3 wherein the absorbent article is bounded by a footprint boundary, and the continuous region is spaced apart from the footprint boundary.

7. The fluid management article of claim 1 wherein the channels are oblique with respect to the longitudinally-extending centerline.

8. The fluid management article of claim 1 wherein a projected area of the protrusions and a projected area of the channels has a ratio between about 3 and 7.

9. The fluid management article of claim 3 wherein the apex of each of the protrusions extends above a reference point outside of the continuous region.

10. The fluid management article of claim 3 wherein the apex of the protrusions resides above a reference point outside of the continuous region, and the channels have a lower surface that resides below the reference point.

11. The fluid management article of claim 10 wherein the lower surface of the channels is a lowermost surface within the continuous region.

12. The fluid management article of claim 1 wherein the projections are mesa-shaped.

13. The fluid-management article of claim 1 wherein the absorbent system comprises a plurality of recesses aligned with the protrusions formed in the surface of the cover.

14. The fluid-management article of claim 1 wherein the absorbent system includes an absorbent core and a transfer layer, wherein the transfer layer contacts the absorbent core, and wherein the transfer is intermediate the absorbent core and the cover layer.

15. The fluid-management article of claim 14 wherein the protrusions are formed through the absorbent core and the transfer layer.

16. The fluid-management article of claim 1 wherein the absorbent system includes portions that contact the barrier layer and portions that are detached from the barrier layer.

17. The fluid-management article of claim 1 wherein the fluid management article has a caliper less than about 3.5 mm.

18. The fluid management article of claim 1 wherein the protrusions are substantially non-elastic.

19. The fluid management article of claim 1 wherein the protrusions have an individual length less than about 70 mm.

20. The fluid management article of claim 1 wherein the protrusions have an individual length between about 2 mm and about 35 mm.

21. The fluid-management article of claim 1 wherein the protrusions are present in a number density greater than about 0.15 protrusions per cm$^2$.

22. The fluid-management article of claim 1 wherein the protrusions are present in a number density between about 0.25 protrusions per cm$^2$ and about 25 protrusions per cm$^2$.

23. The fluid-management article of claim 1 wherein the protrusions are present in a number density between about 1 protrusion per centimeters squared and about 4 protrusions per cm$^2$.

24. The fluid-management article of claim 3 wherein the fluid management article has a stiffness, measured within the continuous region, greater than about 300 grams.

25. The fluid-management article of claim 3 wherein the fluid management article has a stiffness, measured within the continuous region, greater than about 400 grams.

26. The fluid-management article of claim 1 wherein the height of the apex above the channels in a range from about 0.75 mm and about 1.5 mm.

27. The fluid-management article of claim 1 wherein the height of the apex above the channels in a range from about 0.5 mm and a caliper of the article.

28. A fluid management article adapted to be worn adjacent to a pudendal region of a wearer, the article comprising: a body-faceable, liquid-pervious cover having a top surface; a garment-faceable, liquid-impervious barrier; and an absorbent system intermediate the cover and the barrier, wherein the fluid management article comprises a plurality of connected fluid-guiding channels, wherein the fluid-guiding channels surround and thereby isolate a plurality of protrusions, wherein the channels and the protrusions are formed through at least a portion of the absorbent system and into the top surface of the cover, wherein the protrusions have an apex that extends a height greater than about 0.5 mm above at least a portion of a lower surface of the channels, and wherein the protrusions have a number density greater than about 0.15 protrusions/cm$^2$.

* * * * *